United States Patent [19]
Platt

[11] Patent Number: 6,099,860
[45] Date of Patent: Aug. 8, 2000

[54] CONTROLLED RELEASE ORAL PREPARATION WITH NAPROXEN SODIUM AND PSEUDOEPHEDRINE

[76] Inventor: Chris E. Platt, 14352 Riviera St., Huntington Beach, Calif. 92647

[21] Appl. No.: 09/489,396

[22] Filed: Jan. 21, 2000

[51] Int. Cl.⁷ .......................... A61K 31/19; A61K 31/14
[52] U.S. Cl. ..................... 424/465; 514/643; 514/569; 424/464
[58] Field of Search ................................ 424/472, 464, 424/465; 514/569, 643

[56] References Cited

U.S. PATENT DOCUMENTS 4,552,899  11/1985  Sunshine et al. .
4,619,934  10/1986  Sunshine et al. .
5,859,060   1/1999  Platt .
5,998,478  12/1999  Platt .

*Primary Examiner*—Thurman K. Page
*Assistant Examiner*—Amy E Pulliam
*Attorney, Agent, or Firm*—James G. O'Neill

[57] ABSTRACT

Pharmaceutical compositions comprising from about 50 mg to 500 mg of the non-steroidal anti-inflammatory analgesic naproxen and from about 15 mg to 120 mg of the decongestant pseudoephedrine are provided in a controlled release oral preparation suitable for dosing every 12 hours in a therapy or cure of sinusitis, or sinus headaches, generally exemplified by discomfort, pain, pressure, and dizziness.

1 Claim, No Drawings

CONTROLLED RELEASE ORAL PREPARATION WITH NAPROXEN SODIUM AND PSEUDOEPHEDRINE

BACKGROUND OF THE INVENTION

The present invention relates generally to novel pharmaceutical compositions of matter comprising the non-steroidal anti-inflammatory analgesic naproxen in combination with the decongestant pseudoephedrine and appropriate non-toxic carriers and to methods of using such compositions in the therapy or cure of sinusitis, or sinus headaches, generally exemplified by discomfort, pain, pressure, and dizziness.

Non-narcotic analgesics, commonly known as non-steroidal anti-inflammatory drugs, such as naproxen, are widely administered orally in the treatment of mild to severe pain. These drugs have been disclosed as useful in treating cough/cold symptoms in combination with certain antihistamines and decongestants. See, for example U.S. Pat. No. 4,552,899 to Sunshine.

Naproxen as non-steroidal anti-inflammatory pain reliever has greater advantage than other pain relievers acetaminophen, aspirin, and ibuprofen. Naproxen has a significantly greater duration or half-life that leads to twice a day dosage. It is generally accepted that decreased dosing leads to patient convenience and better compliance.

Originally combinations of anti-inflammatories and antihistamines or decongestants were combined with no consideration to the vastly different drug duration or half-lives. These drugs with different half-lives were not combined in a synergistic manner which led the body effectively using them at equal rates. This would lead to ineffective combinations of anti-inflammatories and decongestants and the return of partial symptoms.

SUMMARY OF THE INVENTION

It is a primary object of the present invention to provide a novel timed-release pharmaceutical composition comprising an analgesically effective amount of naproxen and an effective amount of decongestant pseudoephedrine with pharmaceutically acceptable excipients.

It is a further object of the present invention that administration of the disclosed specific ratio of composition optimizes the most effective drug level of both drugs in the body over time for relief for nasal sinus congestion that causes headache pain, pressure, dizziness, and general malaise.

DETAILED DESCRIPTION OF THE INVENTION

More specifically, the applicant herein has found that a controlled release or timed-release combination product suitable for oral administration comprising naproxen and pseudoephedrine combined with or without an appropriate base salt provides improved and unexpected results. Through extensive studies it has been found that the preferred dosage forms disclosed herein provide for immediate release of naproxen and some pseudoephedrine, and specific controlled release or timed release of the remaining pseudoephedrine.

The release of naproxen and pseudoephedrine takes place together up to 12 hours, preferably 10 hours. One or two oral preparations or tablets are administered orally, preferably two. Concentration ranges for the active ingredients are preferably: naproxen, 50–500 mg per tablet and pseudoephedrine 30–240 mg per tablet. The concentration ranges represent about 7–30% of an oral preparation or coated tablet weight of pseudoephedrine and about 15–60% of naproxen.

The preferred dosage form is an oral preparation or coated tablet. In the coated tablet, naproxen and some pseudoephedrine are on the outer coating and thus released immediately while the pseudoephedrine in the core is released over time, preferably over the duration of the half-life of the naproxen, approximately 10 to 12 hours. The outer-coating dissolves rapidly to release both the naproxen and pseudoephedrine therein, while the inner core dissolves slowly to time release pseudoephedrine through hydration and diffusion of the drug from the core polymer. In a controlled release oral preparation there about 50 mg to 500mg of naproxen and about 15 mg to 120mg of pseudoephedrine. The oral preparation has a controlled release matrix comprised of hydrophilic or hydrophobic compounds.

The dosage range for naproxen is from 50–800 mg per day depending upon pain management requirements. The range of pseudoephedrine is between 30–240 mg per day depending on blood pressure values and overall health of the patient. Both drugs will vary depending upon the age and weight of the patient, the severity of the symptoms and the incidence of side effects for humans.

The core in a timed-release tablet or at least a portion of an oral preparation, consists of common hydrophilic swellable polymers such as 25 hydroxypropylmethylcellulose (HPMC) or hydroxypropylcellulose either by themselves or in combination with each other. The hydrated polymers act as a binder that swells when hydrated by gastric media and delays absorption. In a tablet, the combination of polymers will represent about 15% of tablet core weight. The tablet outer coating and/or a portion of the oral preparation comprises HPMC and a plasticizer such as polyethylene 30 glycol (PEG) both which dissolve immediately in gastric fluids. Suitable coloring and flavoring agents may be included.

The tablet core or the oral preparation also includes excipients such as polymers, fillers, binders, lubricants, and antiadherents, all necessary for standard tablet manufacture. Binders are present at a concentration of 5% and typically are starch, gelatin, natural or artificial gums. Fillers are present in the oral preparation and in the tablet. For example, in the tablet at a concentration of about 10 to 20% of tablet core weight and may include starches or cellulose. Antiadherents may be used to prevent oral preparations and tablets from sticking to a device such as a tablet press, and typically include silicas and talc. If present they will be from from 0 to 6% of the oral preparation or tablet core weight. Typical lubricants are magnesium stearate, boric acid, or sodium benzoate at a concentration of about 2.5% to 5% of the tablet core weight. Additional binders used in the granulation of the drug polymer mixture include povidone and corn starch. In tablets, such binders are present at a concentration of about 0.5% to 3% of the tablet core weight.

The means of preparing oral preparations of the present invention, e.g. tablet mixing, compaction, and coating are all well known to those skilled in the art. An example of a tablet is set forth below:

EXAMPLE I

|  | Mg/tablet |
| --- | --- |
| A. Core Tablet | |
| Pseudoephedrine Sulfate | 30 |
| Microcrystalline Cellulose | 140 |
| Povidone | 15 |
| HPMC/PEG | 40 |
| Magnesium Stearate | 10 |

-continued

| | Mg/tablet |
|---|---|
| B. Outer Coating | |
| Naproxen | 100 |
| Pseudoephedrine Sulfate | 30 |
| HPMC/PEG | 10 |

METHOD OF MANUFACTURE

A. Outer Coating
 1. Dissolve HPMC/PEG in an alcohol mixture.
 2. Disperse Naproxen and Pseudoephedrine in the HPMCIPEG solution.
 3. Coat inner tablets below with the solution using standard procedures.

B. Inner Core
 1. Mix pseudoephedrine sulfate, microcrystalline cellulose and HPMC.
 2. Dissolve povidone in an alcoholic mixture and use it to crystallate the powder mix.
 3. Dry pseudoephedrine sulfate crystalate mix.
 4. Compress into tablets.

While the invention is described and illustrated with reference to certain preferred embodiments thereof, those skilled in the art will appreciate that various changes or modifications can be made therein without departing from the spirit of the invention For example, effective dosages of the active ingredients other than the preferred ranges set forth hereinabove may be used. It is intended that the invention be limited only by the scope of the claims that follow.

What is claimed is:

1. A controlled release tablet consisting of a matrix core consisting of about 50 mg to 500 mg naproxen sodium and about 15 mg to 120 mg pseudoephedrine and about 15% of a hydrophilic compound.

* * * * *